(12) United States Patent
Jagger et al.

(10) Patent No.: US 8,439,961 B2
(45) Date of Patent: May 14, 2013

(54) STENT RETAINING MECHANISMS

(75) Inventors: Karl A. Jagger, Deephaven, MN (US); Tracee Eidenschink, Wayzata, MN (US); Derek Sutermeister, Eden Prairie, MN (US); Daniel Gregorich, St. Louis Park, MN (US); Yousef Alkhatib, Maple Grove, MN (US); Matt Heidner, Maple Grove, MN (US); Adam Jennings, Buffalo, MN (US); Richard C. Gunderson, Maple Grove, MN (US); John Blix, Maple Grove, MN (US); Timothy J. Mickley, Elk River, MN (US); Richard Olson, Blaine, MN (US); Jan Weber, Maple Grove, MN (US); Dominick Godin, Mound, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 2004 days.

(21) Appl. No.: 11/496,249

(22) Filed: Jul. 31, 2006

(65) Prior Publication Data

US 2008/0027528 A1    Jan. 31, 2008

(51) Int. Cl.
*A61F 2/06* (2006.01)
(52) U.S. Cl.
USPC .......................................................... 623/1.11
(58) Field of Classification Search .............. 623/1.11, 623/1.12
See application file for complete search history.

(56) References Cited

U.S. PATENT DOCUMENTS

| | | | |
|---|---|---|---|
| 5,250,167 A | 10/1993 | Adolf et al. | 204/299 |
| 5,534,007 A | 7/1996 | St. Germain et al. | 606/108 |
| 5,681,345 A | 10/1997 | Euteneuer | 606/198 |
| 5,683,451 A * | 11/1997 | Lenker et al. | 623/1.11 |
| 5,752,935 A | 5/1998 | Robinson et al. | 604/97 |
| 5,755,685 A | 5/1998 | Andersen | 604/53 |
| 5,788,707 A | 8/1998 | Del Toro et al. | 606/108 |
| 5,855,565 A | 1/1999 | Bar-Cohen et al. | 604/104 |
| 5,873,880 A * | 2/1999 | Williams et al. | 606/108 |
| 5,919,164 A | 7/1999 | Andersen | 604/102 |
| 5,941,871 A | 8/1999 | Adams et al. | 604/523 |
| 5,947,927 A | 9/1999 | Mertens | 604/96 |
| 5,968,069 A | 10/1999 | Dusbabek et al. | 606/194 |

(Continued)

FOREIGN PATENT DOCUMENTS

EP     0819411 A2    2/1998

OTHER PUBLICATIONS

D. Zhou et al., "Actuators for the Cochlear Implant," *Synthetic Metals*, 135-136 (2003) 39-40.

(Continued)

*Primary Examiner* — Gary Jackson
*Assistant Examiner* — Lindsey Bachman
(74) *Attorney, Agent, or Firm* — Vidas, Arrett & Steinkrause, P.A.

(57) ABSTRACT

A catheter system comprises a catheter comprising a distal portion, a proximal portion and an inner shaft. The inner shaft comprises a medical device receiving region for receiving and carrying a medical device. The retaining device is at least partially constructed of an electroactive polymer. The retaining device is located on or adjacent to the medical device receiving region. The electroactive polymer of the retaining device has an activated state and an inactivated state. The retaining device is capable of retaining a medical device to the catheter and releasing the medical device from the catheter by transitioning between the activated state and the inactivated state.

1 Claim, 13 Drawing Sheets

U.S. PATENT DOCUMENTS

| | | | | |
|---|---|---|---|---|
| 6,007,543 | A | 12/1999 | Ellis et al. | 606/108 |
| 6,066,155 | A | 5/2000 | Amann et al. | 606/192 |
| 6,077,295 | A | 6/2000 | Limon et al. | 623/1 |
| 6,096,045 | A | 8/2000 | Del Toro et al. | 606/108 |
| 6,109,852 | A | 8/2000 | Shahinpoor et al. | 414/1 |
| 6,110,180 | A | 8/2000 | Foreman et al. | 606/108 |
| 6,117,296 | A | 9/2000 | Thomson | 204/607 |
| 6,126,685 | A * | 10/2000 | Lenker et al. | 623/1.11 |
| 6,221,097 | B1 | 4/2001 | Wang et al. | 623/1.11 |
| 6,249,076 | B1 | 6/2001 | Madden et al. | 310/363 |
| 6,331,186 | B1 | 12/2001 | Wang et al. | 623/1.11 |
| 6,342,066 | B1 | 1/2002 | Toro et al. | 623/1.11 |
| 6,350,277 | B1 | 2/2002 | Kocur | 623/1.11 |
| 6,388,043 | B1 | 5/2002 | Langer et al. | 528/80 |
| 6,443,880 | B2 | 9/2002 | Blais et al. | 492/16 |
| 6,478,814 | B2 * | 11/2002 | Wang et al. | 623/1.12 |
| 6,514,237 | B1 | 2/2003 | Maseda | 604/533 |
| 6,514,280 | B1 * | 2/2003 | Gilson | 623/1.11 |
| 6,569,192 | B1 | 5/2003 | Foreman et al. | 623/1.11 |
| 6,602,226 | B1 | 8/2003 | Smith et al. | 604/103.05 |
| 6,676,692 | B2 | 1/2004 | Rabkin et al. | 623/1.11 |
| 6,679,836 | B2 | 1/2004 | Couvillon, Jr. | 600/146 |
| 6,682,553 | B1 | 1/2004 | Webler, Jr. | 623/1.11 |
| 6,733,473 | B1 | 5/2004 | Reifart et al. | 604/96.01 |
| 6,749,556 | B2 | 6/2004 | Banik | 600/30 |
| 6,770,027 | B2 | 8/2004 | Banik et al. | 600/146 |
| 6,812,624 | B1 | 11/2004 | Pei et al. | 310/800 |
| 6,835,173 | B2 | 12/2004 | Couvillon, Jr. | 600/146 |
| 6,837,901 | B2 | 1/2005 | Rabkin et al. | 623/1.11 |
| 6,921,360 | B2 | 7/2005 | Banik | 600/30 |
| 6,940,211 | B2 | 9/2005 | Pelrine et al. | 310/330 |
| 6,969,395 | B2 | 11/2005 | Eskuri | 606/200 |
| 6,982,514 | B1 | 1/2006 | Lu et al. | 310/300 |
| 6,984,244 | B2 | 1/2006 | Perez et al. | 623/1.23 |
| 6,997,870 | B2 | 2/2006 | Couvillon, Jr. | 600/146 |
| 7,077,808 | B2 | 7/2006 | Couvillon, Jr. | 600/466 |
| 7,347,868 | B2 * | 3/2008 | Burnett et al. | 623/1.11 |
| 2003/0105508 | A1 * | 6/2003 | Johnson et al. | 623/1.11 |
| 2004/0068161 | A1 | 4/2004 | Couvillon, Jr. | 600/143 |
| 2004/0093063 | A1 | 5/2004 | Wright et al. | 623/1.12 |
| 2004/0102832 | A1 | 5/2004 | Doty | 623/1.11 |
| 2004/0106977 | A1 | 6/2004 | Sullivan et al. | |
| 2004/0143160 | A1 | 7/2004 | Couvillon, Jr. | 600/114 |
| 2004/0148000 | A1 | 7/2004 | Bilge | 623/1.11 |
| 2004/0167564 | A1 | 8/2004 | Fedie | |
| 2004/0172119 | A1 | 9/2004 | Eidenschink | 623/1.11 |
| 2004/0172121 | A1 | 9/2004 | Eidenschink | 623/1.11 |
| 2005/0085693 | A1 | 4/2005 | Belson et al. | 600/146 |
| 2005/0102017 | A1 | 5/2005 | Mattison | 623/1.11 |
| 2005/0107669 | A1 | 5/2005 | Couvillon, Jr. | 600/146 |
| 2005/0119719 | A1 * | 6/2005 | Wallace et al. | 623/1.11 |
| 2005/0149161 | A1 | 7/2005 | Eidenschink et al. | 623/1.11 |
| 2005/0154442 | A1 | 7/2005 | Eidenschink et al. | 623/1.11 |
| 2005/0165439 | A1 | 7/2005 | Weber et al. | 606/191 |
| 2005/0183259 | A1 | 8/2005 | Eidenschink et al. | 29/508 |
| 2005/0228478 | A1 | 10/2005 | Heidner | |
| 2005/0288764 | A1 * | 12/2005 | Snow et al. | 623/1.11 |
| 2006/0041264 | A1 | 2/2006 | Eskuri | 606/153 |
| 2006/0111618 | A1 | 5/2006 | Couvillon, Jr. | 600/152 |

OTHER PUBLICATIONS

E. Smela et al., "Thiol Modified Pyrrole Monomers: 1. Synthesis, Characterization, and Polymerization of 1-(2-Thioethyl)-Pyrrole and 3-(2-Thioethyl)-Pyrrole," *Langmuir*, 14 (11), 2970-2975, 1998.

E.W.H. Jagger, E. Smela, O.Inganas, "Microfabricating Conjugated Polymer Actuators," *Science*, 290, 1540-1545, 2000.

E. Smela, M. Kallenbach, and J. Holdenried, "Electrochemically Driven Polypyrrole Bilayers for Moving and Positioning Bulk Micromachined Silicon Plates," *J. Microelectromechanical Systems*, 8(4), 373-383, 1999.

Madden et al, Proceedings of the SPIE, vol. 4329, 73-83, 2001.

* cited by examiner

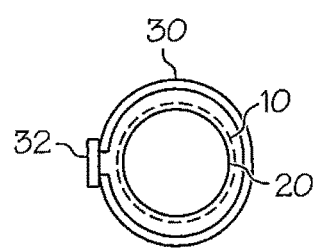
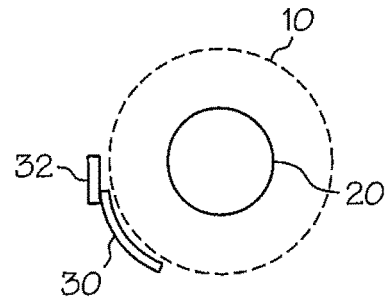
FIG. 5a  FIG. 5b
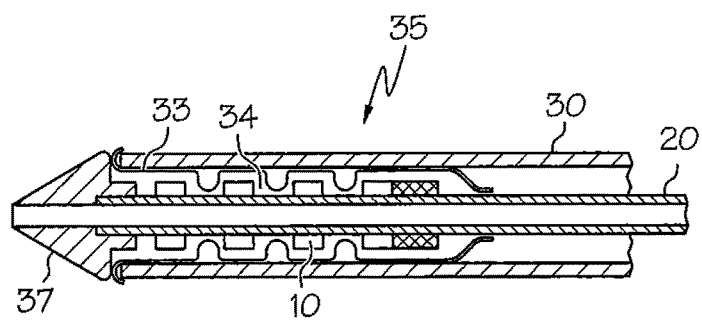
FIG. 6a
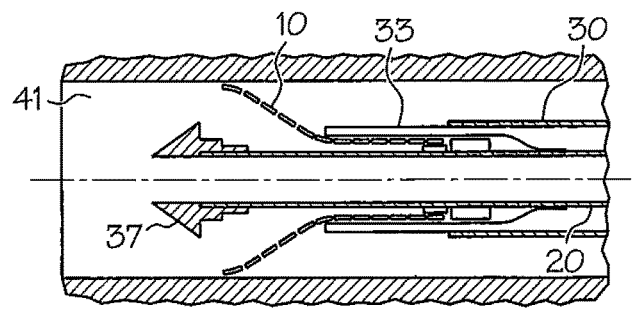
FIG. 6b
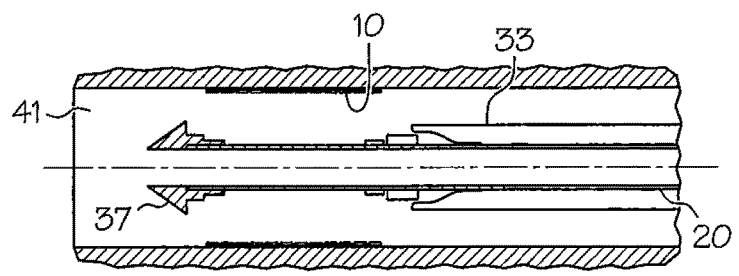
FIG. 6c

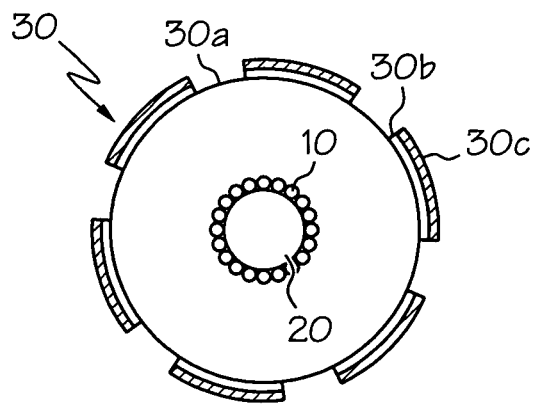 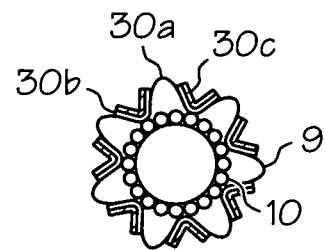
FIG. 7  FIG. 8
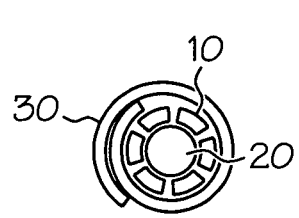 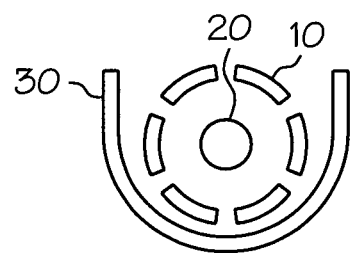
FIG. 9a  FIG. 9b
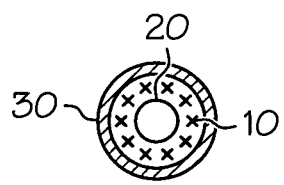 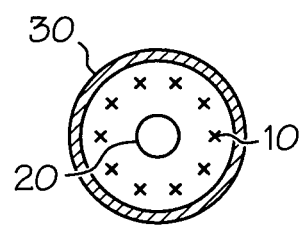
FIG. 10a  FIG. 10b

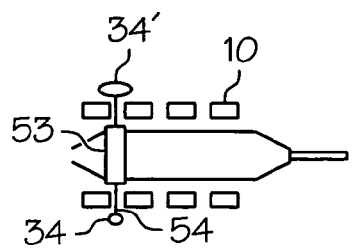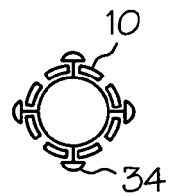
FIG. 19a     FIG. 19b
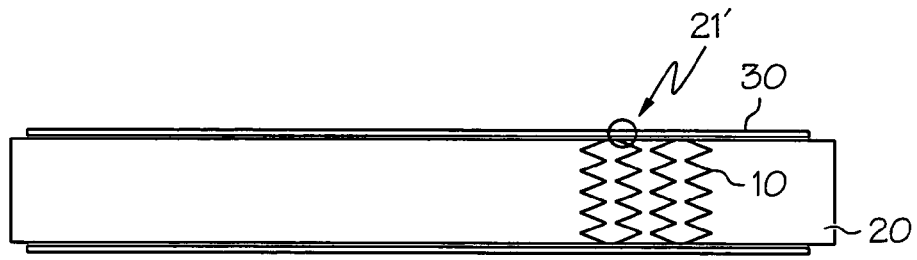
FIG. 20
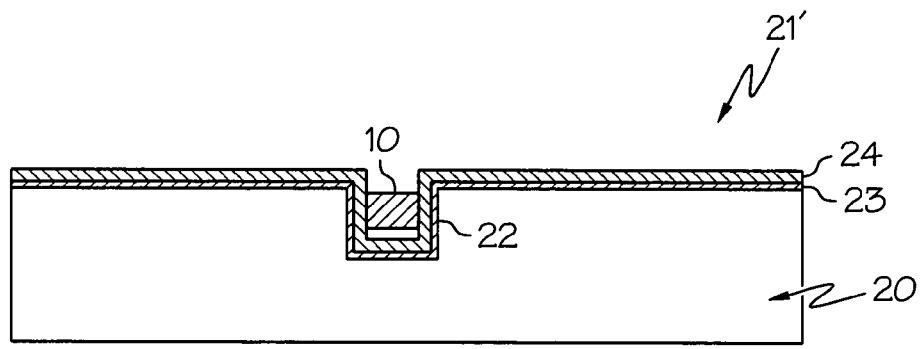
FIG. 21a
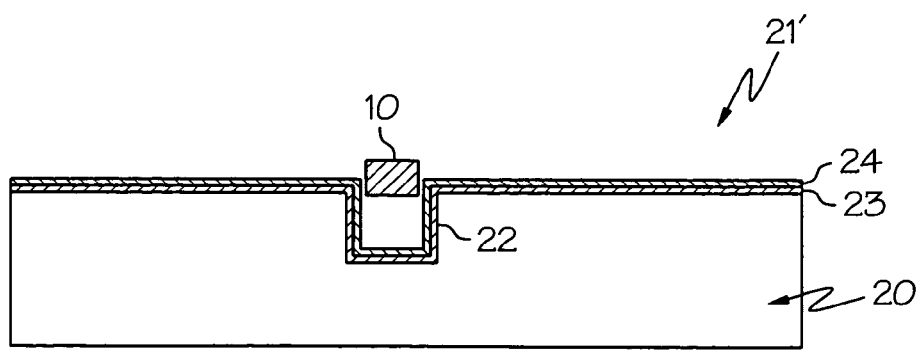
FIG. 21b

STENT RETAINING MECHANISMS

FIELD OF THE INVENTION

This invention relates to an assembly and method for delivering and deploying an expandable medical device, particularly within a lumen of a body vessel. More specifically, this invention relates to the application of electroactive polymers (EAP) on catheter assemblies.

BACKGROUND OF THE INVENTION

Percutaneous transluminal coronary angioplasty (PTCA) is a procedure that is well established for the treatment of blockages, lesions, stenosis, thrombus, etc. present in body lumens such as the coronary arteries and/or other vessels.

A widely used form of percutaneous coronary angioplasty makes use of a dilatation balloon catheter, which is introduced into and advanced, through a lumen or body vessel until the distal end thereof is at a desired location in the vasculature. Once in position across an afflicted site, the expandable portion of the catheter, or balloon, is inflated to a predetermined size with a fluid at relatively high pressures. By doing so the vessel is dilated, thereby radially compressing the atherosclerotic plaque of any lesion present against the inside of the artery wall, and/or otherwise treating the afflicted area of the vessel. The balloon is then deflated to a small profile so that the dilatation catheter may be withdrawn from the patient's vasculature and blood flow resumed through the dilated artery.

In angioplasty procedures of the kind described above, there may be restenosis of the artery, which either necessitates another angioplasty procedure, a surgical by-pass operation, or some method of repairing or strengthening the area. To reduce restenosis and strengthen the area, a physician can implant an intravascular prosthesis for maintaining vascular patency, such as a stent, inside the artery at the lesion.

Stents, grafts, stent-grafts, vena cava filters, expandable frameworks, and similar implantable medical devices, collectively referred to hereinafter as stents, are radially expandable endoprostheses which are typically intravascular implants capable of being implanted transluminally and enlarged radially after being introduced percutaneously. Stents may be implanted in a variety of body lumens or vessels such as within the vascular system, urinary tracts, bile ducts, fallopian tubes, coronary vessels, secondary vessels, etc. They may be self-expanding, expanded by an internal radial force, such as when mounted on a balloon, or a combination of self-expanding and balloon expandable (hybrid expandable).

Prior to delivery a stent or stents may be retained on a portion of the delivery catheter by crimping the stent onto the catheter, retaining the stent in a reduced state about the catheter with a removable sheath, sleeve, sock or other member or members, or by any of a variety of retaining mechanisms or methods. Some examples of stent retaining mechanisms are described in U.S. Pat. No. 5,534,007; U.S. Pat. No. 5,681,345; U.S. Pat. No. 5,788,707; U.S. Pat. No. 5,968,069; U.S. Pat. No. 6,066,155; U.S. Pat. No. 6,096,045; U.S. Pat. No. 6,221,097; U.S. Pat. No. 6,331,186; U.S. Pat. No. 6,342,066; U.S. Pat. No. 6,350,277; U.S. Pat. No. 6,443,880; and U.S. Pat. No. 6,478,814.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

BRIEF SUMMARY OF THE INVENTION

The present invention is directed to variations of catheter systems, supplemented with electroactive polymer (EAP) material to modify the performance characteristics of the catheter. At least some embodiments are directed to catheter systems wherein EAP material is utilized in one or more mechanisms of a catheter for retaining and/or delivering a stent.

In at least one embodiment a catheter system comprises a catheter, a stent, and retaining device at least partially constructed of an electroactive polymer. The catheter has a distal portion, a proximal portion and an inner shaft. The inner shaft includes a medical device receiving region for receiving and carrying a medical device. A stent can be disposed about the medical device receiving region and can have a reduced state and an expanded state. In the reduced state the stent can be retained about the device receiving region while in the expanded state the stent can be released from the device receiving region. The retaining device can be at least partially constructed of an electroactive polymer and can be located at the medical device receiving region. The retaining device can retain or assist in retaining the stent in the reduced state and can release the stent in the expanded state. The electroactive polymer of the retaining device can have a first shape in the activated state and a second shape in the inactivated state wherein the first shape and the second shape are different from one another.

These and other embodiments which characterize the invention are pointed out with particularity in the claims annexed hereto and forming a part hereof. However, for a better understanding of the invention, its advantages and objectives obtained by its use, reference should be made to the drawings which form a further part hereof and the accompanying descriptive matter, in which there is illustrated and described embodiments of the invention.

BRIEF DESCRIPTION OF THE SEVERAL VIEWS OF THE DRAWING(S)

A detailed description of the invention is hereafter described with specific reference being made to the drawings.

FIG. 5a is a cross-sectional view of a catheter with a sheath retaining a stent.

FIG. 5b is a cross-sectional view of a catheter with a sheath with an expanded stent.

FIG. 6a is a side view of a catheter with a sheath comprising a rolling membrane coated with an electroactive polymer.

FIG. 6b is a side view of a catheter with a partially retracted sheath comprising a rolling membrane disposed within a body lumen.

FIG. 6c is a side view of a catheter with a fully retracted sheath comprising a rolling membrane disposed within a body lumen.

FIGS. 7-8 are cross-sectional views of a catheter with a sheath having electroactive polymer that expands and contracts the sheath.

FIGS. 9a-b are side views of a catheter with a sheath which rolls about a stent.

FIGS. 10a-b are cross-sectional views of a catheter with an EAP sheath which when activated produces a larger interior diameter.

Figure 10C:
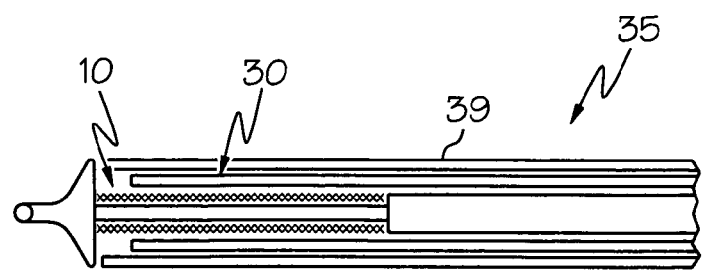
Figure 10D:
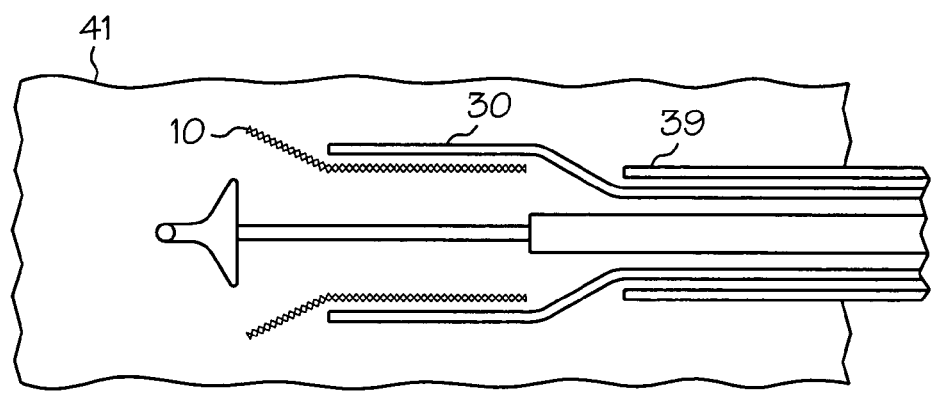
Figure 10E:
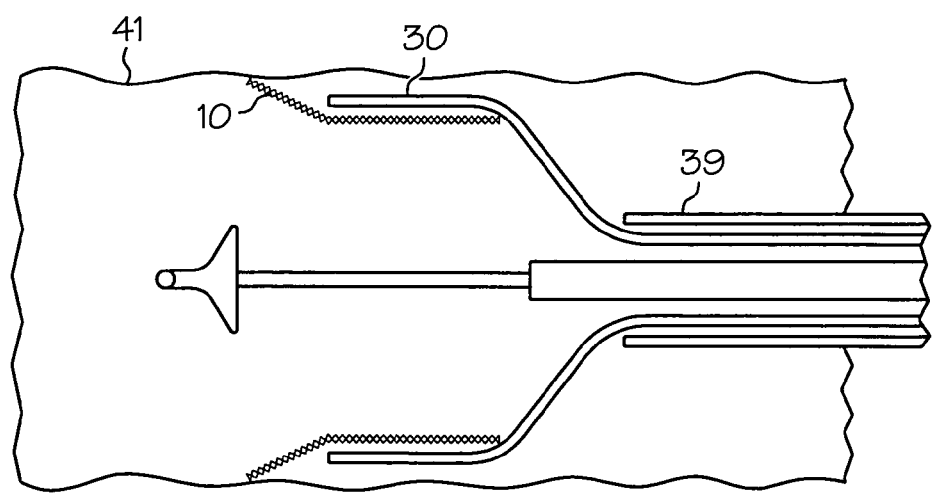

FIGS. 10c-e are side views of a catheter with one sheath disposed about an EAP sheath.

Figure 11A:
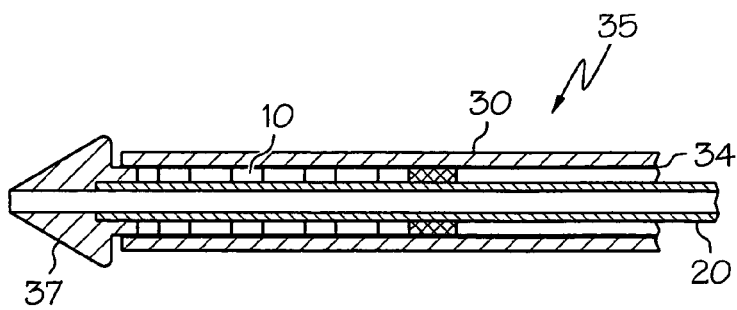

FIG. 11a is a side view of a catheter with a sheath disposed about the length of the stent.

Figure 11B:
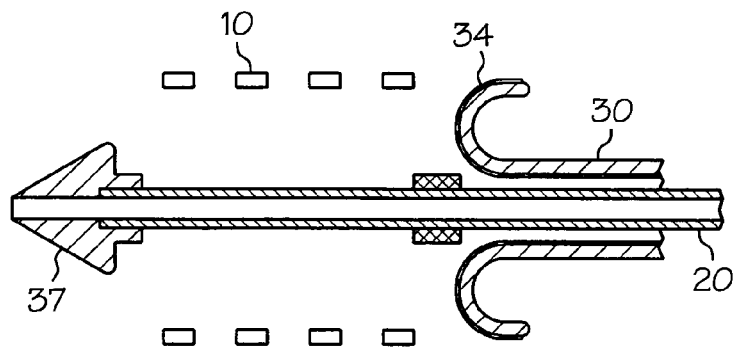

FIG. 11b is a side view of a catheter with a sheath retracted from about the stent.

Figure 12A:
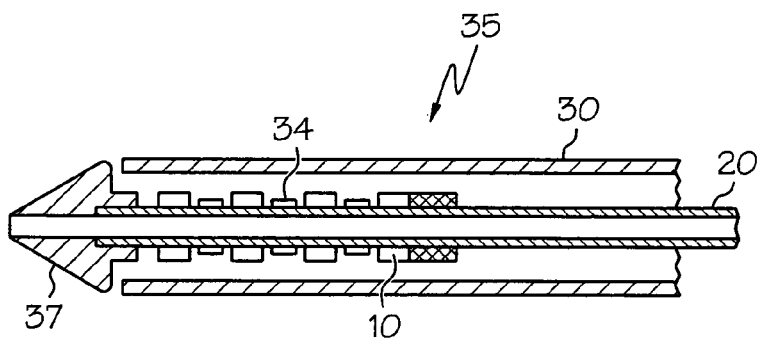
Figure 12B:
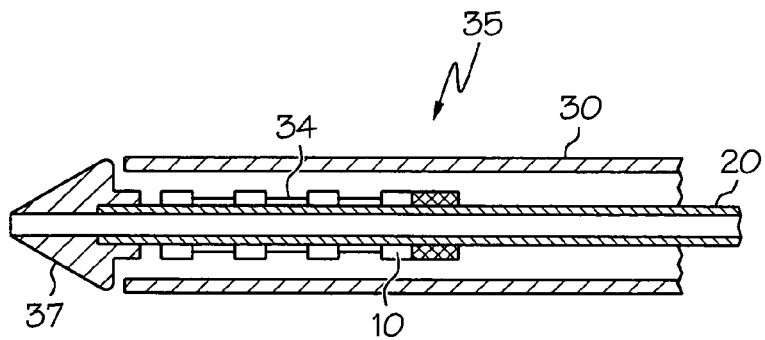

FIGS. 12a-b are side views of a catheter with portions of EAP disposed about the inner shaft and between stent struts.

Figure 13A:
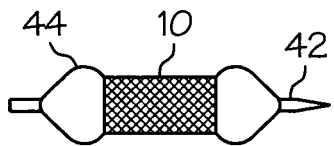
Figure 13B:
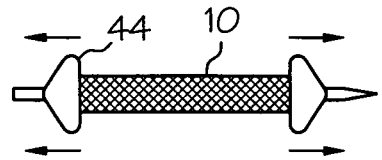
Figure 13C:
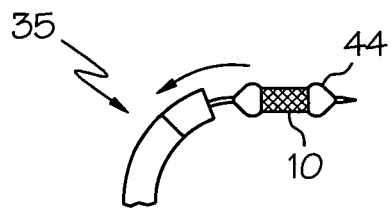

FIGS. 13a-c are side views of a catheter with a sock comprising an EAP portion for retaining a stent.

Figure 14A:
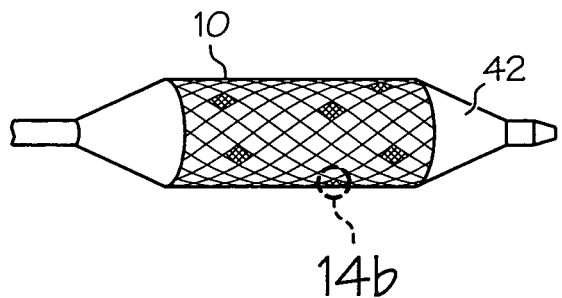
Figure 14B:
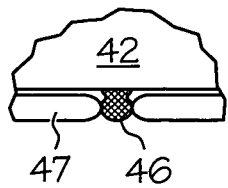
Figure 14C:
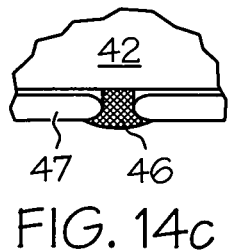

FIGS. 14a-c are side views of a catheter with at least one stent retaining portion retaining a stent.

FIGS. 15a-e are side views of a catheter with the retaining device comprising a hook and loop configuration.

Figure 16A:
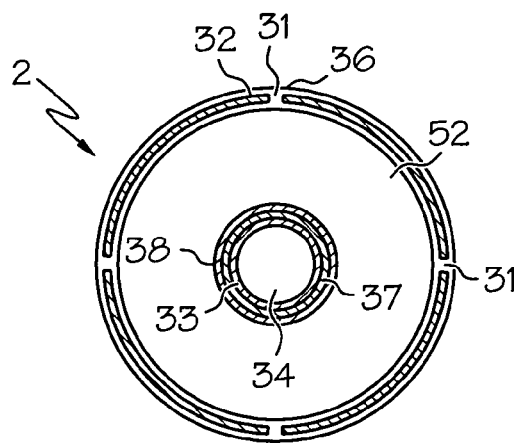

FIG. 16a is a cross-sectional view of a catheter with an electroactive polymer ring inside a retaining sheath.

Figure 16B:
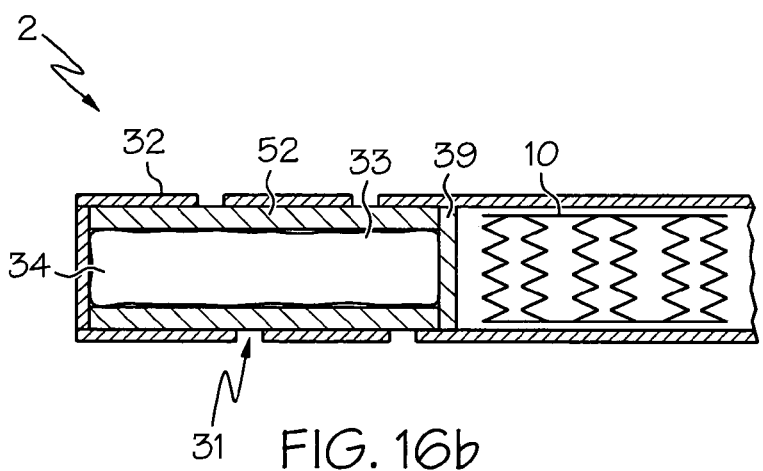
Figure 16C:
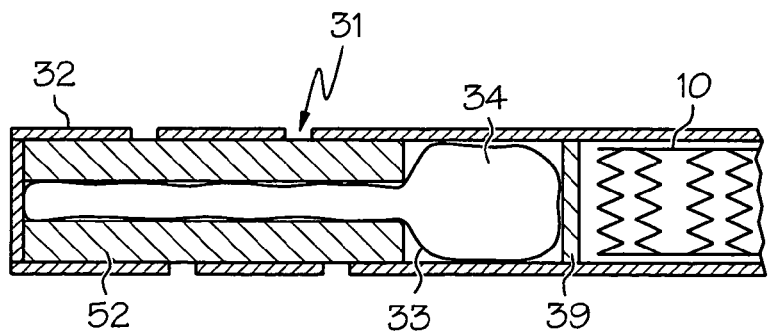

FIGS. 16b-c are side views of a catheter with a catheter tip at least partially constructed of an electroactive polymer cylinder disposed about the catheter tip.

Figure 17A:
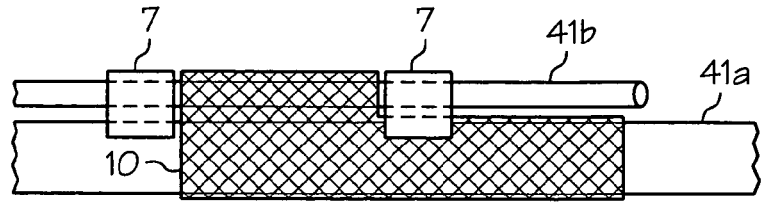

FIGS. 17a,c are side views of a catheter with an EAP sock or EAP bumpers in the main branch as well as the side branch of the stent.

Figure 17B:

FIGS. 17b,d are cross sectional views across the longitudinal of an EAP sock or EAP bumper used on the main branch as well as the side branch of the stent.

FIGS. 17e-h are partial side views of a catheter with an EAP sock or EAP bumper on the main branch as well as the side branch of the stent.

Figure 18A:
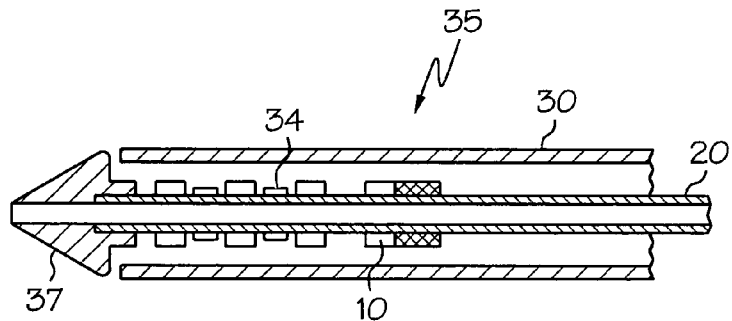
Figure 18B:
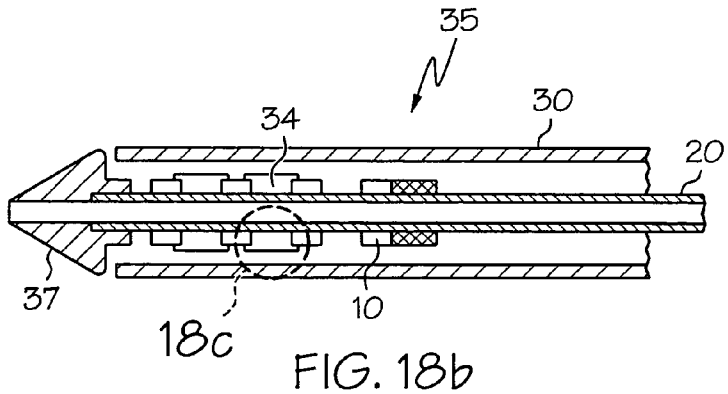
Figure 18C:
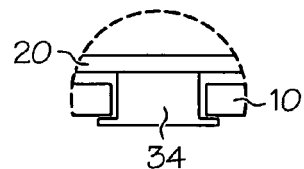

FIGS. 18a-c are side views of a catheter with an electroactive polymer that mushrooms through the cells of the stent.

FIG. 19a is a side view of a catheter with an electroactive polymer head that expands.

FIG. 19b is a side view of a catheter with an electroactive polymer head that expands.

FIGS. 20-21b are side views of a catheter with a pseudo stent pattern engraved in the medical device region.

Figure 22A:
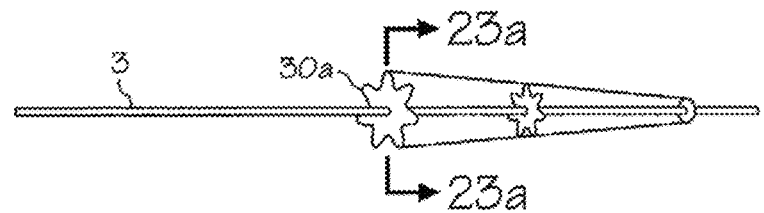
Figure 22B:
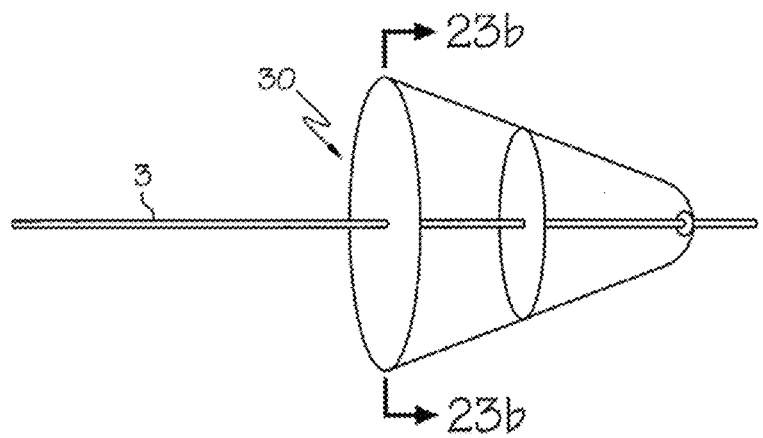

FIGS. 22a-b are side views of a catheter with an EAP umbrella disposed distal of the stent.

Figure 23A:
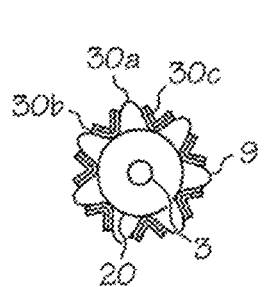
Figure 23B:
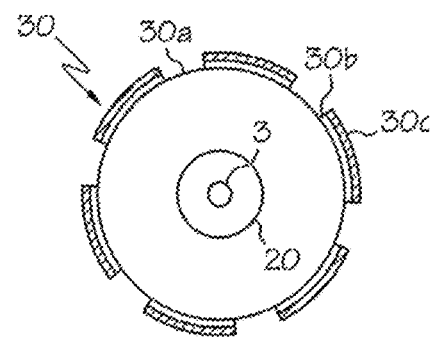

FIGS. 23a-b are cross-sectional views of a catheter with an EAP umbrella disposed distal of the stent.

Figure 24A:
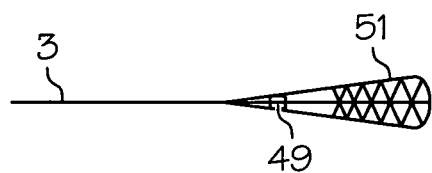
Figure 24B:
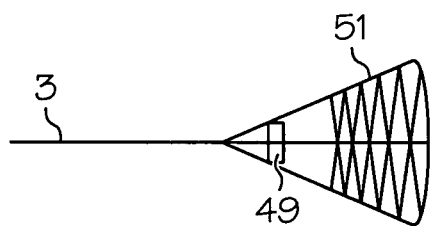

FIG. 24a-b are side views of a catheter with an EAP filter.

DETAILED DESCRIPTION OF THE INVENTION

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Depicted in the figures are various aspects of the invention. Elements depicted in one figure may be combined with, or substituted for, elements depicted in another figure as desired.

The present invention relates to strategic placement or use of electroactive polymers (EAP). Depending on the placement of EAP, a variety of characteristics may be manipulated and/or improved. Particular portions of the catheter configurations of the present invention may be actuated, at least in part, with electroactive polymer (EAP) actuators. Electroactive polymers are characterized by their ability to change shape and/or volume in response to electrical stimulation. EAPs include electric EAPs and ionic EAPs. Piezoelectric materials may also be employed but tend to undergo small deformation when voltage is applied.

Electric EAPs include ferroelectric polymers, dielectric EAPs, electrorestrictive polymers such as the electrorestrictive graft elastomers and electro-viscoelastic elastomers, and liquid crystal elastomer materials.

Ionic EAPs include ionic polymer gels, ionomeric polymer-metal composites, conductive polymers and carbon nanotubes. Upon application of a small voltage, ionic EAPs may bend significantly. Ionic EAPs also have a number of additional properties that make them attractive for use in the devices of the present invention, including the following: (a) they are lightweight, flexible, small and easily manufactured; (b) energy sources are available which are easy to control, and energy may be easily delivered to the EAPS; (c) small changes in potential (e.g., potential changes on the order of 1V) may be used to effect shape and/or volume change in the EAPs; (d) they are relatively fast in actuation (e.g., full expansion/contraction in a few seconds); (e) EAP regions may be created using a variety of techniques, for example, electrodeposition; and (f) EAP regions may be patterned, for example, using photolithography, if desired, or other masking techniques.

Conductive plastics may also be employed to carry current to the EAP. Conductive plastics include common polymer materials which are almost exclusively thermoplastics that require the addition of conductive fillers such as powdered metals or carbon (usually carbon black or fiber).

Ionic polymer gels are activated by chemical reactions and may become swollen upon a change from an acid to an alkaline environment.

Ionomeric polymer-metal composites may bend as a result of the mobility of cations in the polymer network. Suitable base polymers include perfluorosulfonate and perfluorocarboxylate.

Essentially any electroactive polymer that exhibits contractile or expansile properties may be used in connection with the various active regions of the invention, including any of those listed above.

In some embodiments herein, the EAPs employed are ionic EAPs, more specifically, the ionic EAPs are conductive polymers that feature a conjugated backbone (they include a backbone that has an alternating series of single and double carbon-carbon bonds, and sometimes carbon-nitrogen bonds, i.e. π-conjugation) and have the ability to increase the electrical conductivity under oxidation or reduction. For polymers allow freedom of movement of electrons, therefore allowing the polymers to become conductive. The pi-conjugated polymers are converted into electrically conducting materials by oxidation (p-doping) or reduction (n-doping).

The volume of these polymers changes dramatically through redox reactions at corresponding electrodes through exchanges of ions with an electrolyte. The EAP-containing active region contracts or expands in response to the flow of ions out of, or into, the same. These exchanges occur with small applied voltages and voltage variation may be used to control actuation speeds.

Any of a variety of pi-conjugated polymers may be employed herein. Examples of suitable conductive polymers include, but are not limited to, polypyrroles, polyanilines, polythiophenes, polyethylenedioxythiophenes, poly(p-phenylenes), poly(p-phenylene vinylenes), polysulfones, polypyridines, polyquinoxalines, polyanthraquinones, poly(N-vinylcarbazoles) and polyacetylenes, with the most common being polythiophenes, polyanilines, and polypyrroles.

Some of the structures are shown below:

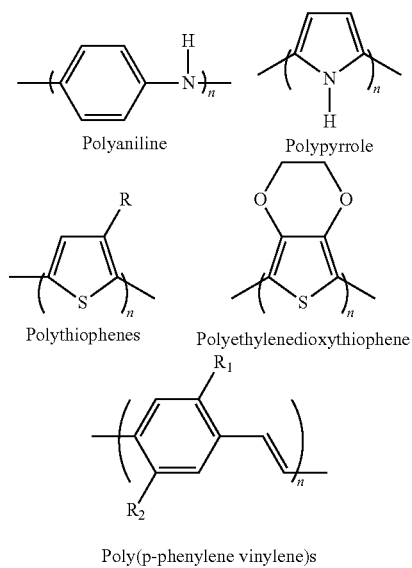

Polypyrrole, shown in more detail below, is one of the most stable of these polymers under physiological conditions:

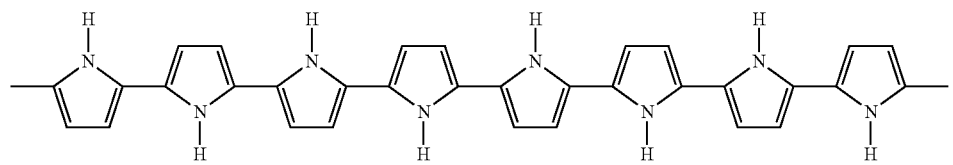

The above list is intended for illustrative purposes only, and not as a limitation on the scope of the present invention.

The behavior of conjugated polymers is dramatically altered with the addition of charge transfer agents (dopants). These materials may be oxidized to a p-type doped material by doping with an anionic dopant species or reducible to a n-type doped material by doping with a cationic dopant species. Generally, polymers such as polypyrrole (PPy) are partially oxidized to produce p-doped materials:

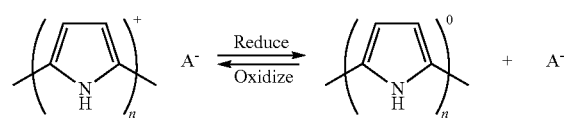

Dopants have an effect on this oxidation-reduction scenario and convert semi-conducting polymers to conducting versions close to metallic conductivity in many instances. Such oxidation and reduction are believed to lead to a charge imbalance that, in turn, results in a flow of ions into or out of the material. These ions typically enter/exit the material from/into an ionically conductive electrolyte medium associated with the electroactive polymer. One dopant that can be used is (trifluoromethanesulfonyl)imide (TFSI). Aqueous or PC solutions can be used as the electrolyte medium. In some embodiments, $H_2O$/PC mixed solutions of LiTFSI are used.

Dimensional or volumetric changes may be effectuated in certain polymers by the mass transfer of ions into or out of the polymer. This ion transfer is used to build conductive polymer actuators (volume change). For example, in some conductive polymers, expansion is believed to be due to ion insertion between chains, whereas in others inter-chain repulsion is believed to be the dominant effect. Regardless of the mechanism, the mass transfer of ions into and out of the material leads to an expansion or contraction of the polymer, delivering significant stresses (e.g., on the order of 3-5 MPa) and strains (e.g., on the order of up to 40%). These characteristics are ideal for construction of the devices of the present invention. As used herein, the expansion or the contraction of the active region of the device is generally referred to as "actuation."

The following elements are commonly utilized to bring about electroactive polymer actuation: (a) a source of electrical potential, (b) an active region, which comprises the electroactive polymer, and (c) a counter electrode. In an ionic electroactive polymer actuation an electrolyte in contact with both the active region and the counter electrode can be used.

The source of electrical potential for use in connection with the present invention may be quite simple, consisting, for example, of a dc battery and an on/off switch. Alternatively, more complex systems may be utilized. For example, an electrical link may be established with a microprocessor, allowing a complex set of control signals to be sent to the EAP-containing active region(s).

The electrolyte, which is in contact with at least a portion of the surface of the active region, allows for the flow of ions and thus acts as a source/sink for the ions. Any suitable electrolyte may be employed herein. The electrolyte may be, for example, a liquid, a gel, or a solid, so long as ion movement is permitted. Examples of suitable liquid electrolytes include, but are not limited to, an aqueous solution containing a salt, for example, an NaCl solution, a KCl solution, a sodium dodecylbenzene sulfonate solution, a phosphate buffered solution, physiological fluid, etc. Examples of suitable gel electrolytes include, but are not limited to, a salt-containing agar gel or polymethylmethacrylate (PMMA) gel. Solid electrolytes include ionic polymers different from the EAP and salt films.

The counter electrode may be formed from any suitable electrical conductor, for example, a conducting polymer, a conducting gel, or a metal, such as stainless steel, gold or platinum. At least a portion of the surface of the counter electrode is generally in contact with the electrolyte, in order to provide a return path for charge.

In one specific embodiment, the EAP employed is polypyrrole. Polypyrrole-containing active regions may be fabricated using a number of known techniques, for example, extrusion, casting, dip coating, spin coating, or electro-polymerization/deposition techniques. Such active regions may also be patterned, for example, using lithographic techniques, if desired.

As a specific example of a fabrication technique, polypyrrole may be galvanostatically deposited on a platinised substrate from a pyrrole monomer solution using the procedures described in D. Zhou et al., "Actuators for the Cochlear Implant," *Synthetic* Metals 135-136 (2003) 39-40. Polypyrrole may also be deposited on gold. In some embodiments, adhesion of the electrodeposited polypyrrole layer is enhanced by covering a metal such as gold with a chemisorbed layer of molecules that may be copolymerized into the polymer layer with chemical bonding. Thiol is one example of a head group for strong chemisorbtion to metal. The tail group may be chemically similar to structured groups formed in the specific EAP employed. The use of a pyrrole ring attached to a thiol group (e.g., via a short alkyl chain) is an example for a polypyrrole EAP. Specific examples of such molecules are 1-(2-thioethyl)-pyrrole and 3-(2-thioethyl)-pyrrole. See, e.g., E. Smela et al., "Thiol Modified Pyrrole Monomers: 1. Synthesis, Characterization, and Polymerization of 1-(2-Thioethyl)-Pyrrole and 3-(2-Thioethyl)-Pyrrole," *Langmuir,* 14 (11), 2970-2975, 1998.

Various dopants may be used in the polypyrrole-containing active regions, including large immobile anions and large immobile cations. According to one specific embodiment, the active region comprises polypyrrole (PPy) doped with dodecylbenzene sulfonate (DBS) anions. When placed in contact with an electrolyte containing small mobile cations, for example, $Na^+$ cations, and when a current is passed between the polypyrrole-containing active region and a counter electrode, the cations are inserted/removed upon reduction/oxidation of the polymer, leading to expansion/contraction of the same. This process may be represented by the following equation:

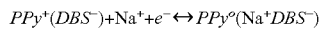

$$PPy^+(DBS^-) + Na^+ + e^- \leftrightarrow PPy^\circ(Na^+DBS^-)$$

where $Na^+$ represents a sodium ion, $e^-$ represents an electron, $PPy^+$ represents the oxidized state of the polypyrrole, $PPy^\circ$ represents the reduced state of the polymer, and species are enclosed in parentheses to indicate that they are incorporated into the polymer. In this case the sodium ions are supplied by the electrolyte that is in contact with the electroactive polymer member. Specifically, when the EAP is oxidized, the positive charges on the backbone are at least partially compensated by the $DBS^-$ anions present within the polymer. Upon reduction of the polymer, however, the immobile $DBS^-$ ions cannot exit the polymer to maintain charge neutrality, so the smaller, more mobile, $Na^+$ ions enter the polymer, expanding the volume of the same. Upon re-oxidation, the $Na^+$ ions again exit the polymer into the electrolyte, reducing the volume of the polymer.

EAP-containing active regions may be provided that either expand or contract when an applied voltage of appropriate value is interrupted depending, for example, upon the selection of the EAP, dopant, and electrolyte.

Additional information regarding EAP actuators, their design considerations, and the materials and components that may be employed therein, may be found, for example, in E. W. H. Jager, E. Smela, O. Inganäs, "Microfabricating Conjugated Polymer Actuators," *Science,* 290, 1540-1545, 2000; E. Smela, M. Kallenbach, and J. Holdenried, "Electrochemically Driven Polypyrrole Bilayers for Moving and Positioning Bulk Micromachined Silicon Plates," *J. Microelectromechanical Systems,* 8(4), 373-383, 1999; U.S. Pat. No. 6,249,076, assigned to Massachusetts Institute of Technology, and *Proceedings of the SPIE,* Vol. 4329 (2001) entitled "Smart Structures and Materials 2001: Electroactive Polymer and Actuator Devices (see, e.g., Madden et al, "Polypyrrole actuators: modeling and performance," at pp. 72-83), each of which is hereby incorporated by reference in its entirety.

Furthermore, networks of conductive polymers may also be employed. For example, it has been known to polymerize pyrrole in electroactive polymer networks such as poly(vinylchloride), poly(vinyl alcohol), NAFION®, a perfluorinated polymer that contains small proportions of sulfonic or carboxylic ionic functional groups, available from E.I. DuPont Co., Inc. of Wilmington, Del.

Electroactive polymers are also discussed in detail in commonly assigned copending U.S. patent application Ser. No. 10/763,825, the entire content of which is incorporated by reference herein. Further information regarding EAP may be found in U.S. Pat. No. 6,514,237, the entire content of which is incorporated by reference herein.

Exposure of anions to the EAP material may cause expansion in a longitudinal dimension. Alternatively, exposure of anions to the EAP material may cause a change in the arcuate direction or orientation of the material. The radius of the arcuate curvature may be as small as a few μm. Exposure of anions to the EAP material may cause the volume and/or length, width, and height dimension of the EAP material to enlarge.

The extent of the expansion of the EAP material in a specific direction can vary from 0.1% to 40% of the original size in that direction following exposure to anions. In some embodiments this is a change of between a micrometer to several millimeters. The speed of the EAP material for expansion or contraction may vary between less than 0.5 seconds to approximately 10 seconds per cycle. The speed of the EAP expansion or contraction is generally dependent upon the access and mobility of the ions flowing in or out of the EAP and as such dependent on the specific shape and porosity of the EAP, together with other physical parameters such as type of ions (size and charge), temperature, viscocity, etc. Thinner EAP materials expand and/or contract at an increased rate as compared to thicker EAP materials.

Generally a voltage of −1.5 to 1.5 volts is utilized to provide the desired anions or cations for implementation of a state change for the EAP into either a pre-delivery or delivery state.

The invention pertains to a catheter system comprising a catheter and a retaining device at least partially constructed of an electroactive polymer. The catheter has a distal portion, a proximal portion and an inner shaft. The inner shaft includes a medical device receiving region for receiving and carrying a medical device. The retaining device is located on or adjacent to the medical device receiving region. The electroactive polymer of the retaining device has an activated state and an inactivated state. The retaining device is capable of retaining a medical device to the catheter and releasing the medical device from the catheter by transitioning between the activated state and the inactivated state.

In at least one embodiment the retaining device may be at least one hub. In at least one embodiment a hub may be located under an inflation balloon. In at least one embodiment a hub may be located at the proximal end of the stent retaining region and at least one other hub may be located at the distal end of the stent retaining region. In at least one embodiment the hubs may be capable of protecting a medical device from low force trauma.

In at least one embodiment the retaining device may be a flexible radiopaque band.

In at least one embodiment the retaining device may be at least one sheath.

In at least one embodiment at least one sheath may be capable of breaking to release the medical device from the catheter.

In at least one embodiment, at least one sheath may comprise a rolling membrane coated with an electroactive polymer.

In at least one embodiment, at least one sheath may comprise at least one electroactive polymer that expands and contracts the sheath as at least one electroactive polymer transitions between activation and inactivation.

In at least one embodiment, at least one sheath may be in the form of a sheet capable of being rolled about a stent in an inactived state and capable of unrolling from about the stent in the activated state.

In at least one embodiment, at least one sheath may have a second sheath disposed thereabout such that upon removal of the second sheath the remaining sheath(s) allows partial expansion of the stent in the inactivated state and full deployment in the activated state.

In at least one embodiment, at least one sheath may be disposed about the length of the stent in the inactivated state and roll off the stent when activated.

In at least one embodiment, the retaining device may be disposed about the inner shaft of the catheter and retain the stent in the inactivated state and deploy the stent in the activated state.

In at least one embodiment, the retaining device may retain the stent in the inactivated state and release the stent in the activated state In at least one embodiment, the retaining device may comprise a hook and loop configuration.

In at least one embodiment, the retaining device may comprise an electroactive polymer ring inside a retaining sheath. The ring may be constructed and arranged to push a stent out of the retaining sheath when in the activated state.

In at least one embodiment, the retaining device may comprise a catheter tip at least partially constructed of an electroactive polymer and a ring disposed about the catheter tip. The ring may be constructed and arranged to slide on the catheter tip such that when the ring is pulled toward the stent and the catheter tip is activated the stent is braced to prevent jumping.

In at least one embodiment, the retaining device may comprise an EAP sock or EAP bumpers. The EAP socks or bumpers may be used for the mainbranch as well as the side branch of the stent and/or catheter.

In at least one embodiment, an EAP opening mechanism for distal protection of the system may be used rather than Nitinol. This may avoid the use of a recovery sheath.

In at least one embodiment, an electroactive polymer may also be used inn the mounting region to engage the stent when the stent is loaded. The stent may then be released upon inactivation of the Eap. In at least one embodiment this may be accomplished by mushrooming the EAP through the cells of the stent.

In at least one embodiment, a pseudo stent pattern may be engraved in the medical device region and EAP segments may be included in areas where stent is to be positioned.

In at least one embodiment, an EAP umbrella may be disposed distal of the stent. The EAP umbrella may then be activated before release to form a bumper in the vessel to prevent the stent from jumping past.

In at least one embodiment, the EAP stent sheath cover is thin such that when activated it expands and then breaks. In at least one embodiment, multiple rings may be used to allow deployment of different portions of the stent.

In at least one embodiment, EAP clamps or other devices may be used to retain the stent.

In at least one embodiment, an EAP sheath when activated grows to reduce withdrawal forces at the lesion site. A larger interior diameter will tend to reduce tendency of the stent to jump.

In at least one embodiment, a retractable sheath of a catheter is supplemented with EAP material to provide active regions comprising electroactive polymer material. When activated, the EAP material radially expands the distal sheath to reduce deployment forces when it is retracted from over the stent. The EAP material is oriented in a pattern such that when the EAP material expands, it increases the diameter of the distal sheath to lessen the friction between the distal sheath and the loaded stent.

In at least one embodiment, a retraction sheath of a catheter is supplemented with EAP material to provide active regions comprising electroactive polymer material. When activated, the EAP material longitudinally contracts or shortens the retraction sheath to withdraw a distal sheath from over the loaded stent.

In at least one embodiment, the proximal end of a distal sheath treated with EAP is fixed to allow for the longitudinal shortening of the distal sheath. The EAP material is oriented in a pattern such that when the EAP material is activated, it decreases the length of the distal sheath, withdrawing it from over the loaded stent.

In at least one embodiment, the proximal end of a retraction sheath treated with EAP is fixed to allow for the longitudinal shortening of the retraction sheath. The EAP material is oriented in a pattern such that when the EAP material is activated, it decreases the length of the retraction sheath to withdraw the distal sheath and release the stent.

In some embodiments, the EAP may be formed of either an electroactive polymer or an anionic electroactive polymer.

In at least one embodiment, the EAP is electrically engaged and is in electrical communication with a source of anions.

In certain other embodiments, the medical devices of the present invention are actuated, at least in part, using materials involving piezoelectric, electrostrictive, and/or Maxwell stresses.

In one embodiment of the invention, the EAP portion of the catheter can be actuated by a current passing through an electrolyte solution from a source of electrical potential. The current can also pass directly to the EAP through an insulated wire, fiber or the like structure of any suitable electrical conductor.

In the various embodiments illustrated in the Figures, the current source for activation of the EAP portion is typically not shown. For such embodiments it typically will be sufficient to provide a metallized layer in contact with a portion of the EAP, to connect the metallized layer to a suitable power source, and to use in situ bodily fluid or an injected saline or physiological saline solution as the electrolyte. A suitable metallized layer material is gold which also has the advantage that is also radioopaque and so the location of the coated EAP component can easily be monitored by fluoroscopy. Other metals however may also be used, for instance stainless steel or platinium, and in some cases conductive polymers or fluids may also provide acceptable performance. To complete an activation circuit for the EAP component the associated catheter or like device may be provided with a counter electrode at any convenient location which brings it into contact with the electrolyte. In some cases an external electrode or ground connection that contacts the skin of the treatment subject may suffice to complete the EAP activation circuit. It should also be understood that the direction of current flow will depend upon the particular design of the device, that is, on whether it is desired to expand or contract the EAP component by direct ions into or out of the EAP material, and that appropriate connections to a power source should be provided accordingly.

Figure 1:
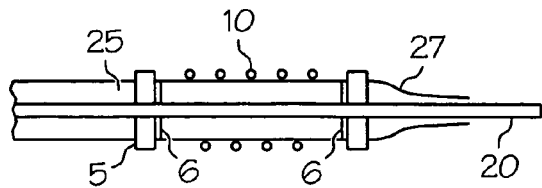
FIG. 1 is a side view of a catheter having a hub retaining the stent.

As shown in FIG. 1, the retaining device can be at least one hub 5 that includes an EAP portion 6 attached to the hub and/or a portion integral to the hub 5. The hub(s) 5 retain a stent 10 or other medical device to a catheter 20. This may be, for instance, by applying pressure on the ends of the stent 10 and/or by overlapping a portion of a hub 5 over the stent 10. Upon activation of the EAP portion the hub 5 can change shape such that the stent 10 is free to expand. Conversely, the stent 10 can be retained in the activated state and released when the EAP portion is inactivated. The hub 5 can also expand in response to activation/inactivation such that the balloon 25 can expand to expand the stent 10. The hubs 5, having EAP material integral or attached to the hubs, can also be constructed of material that accommodates balloon expansion so as to expand the stent 10. The balloon 25 and hubs 5 can also be designed such that upon expansion of the balloon 25 the hubs slide down the cone portions 27 of the balloon.

Figure 2:
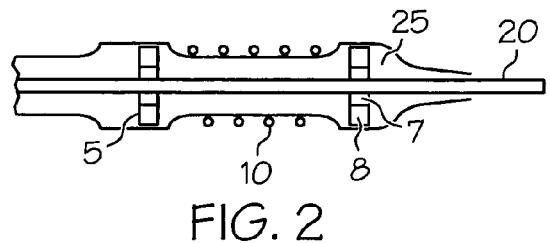
FIG. 2 is a side view of a catheter with a hub located under the balloon.

A hub 5 may be located under the expansion balloon 25 as shown in FIG. 2. The hubs here include a radiopaque portion 7 and an EAP portion 8. The radiopaque portion can comprise a flexible band. In this embodiment, the collapsed configuration of the balloon around the hub provides for stent engagement. A change in the hub configuration can be employed to release the stent.

The hubs 5 in FIGS. 1-2 can also be employed to protect the ends of the stent 10. The hubs 5 can increase or decrease in diameter upon the EAP portion 8 passing between an activated/inactivated state. The hub 5 when tracking can be activated and made larger than is shown if the hub is not crossing a lesion within a body vessel. When crossing a lesion the hub can be inactivated so as to present a smaller profile. Likewise, when the hub 5 is small and the stent 10 is getting hung up within the lumen, the EAP portion 8 of the hub 5 can be activated in order to enlarge the hub diameter thereby protecting the stent 10 from low force trauma.

Figure 3:
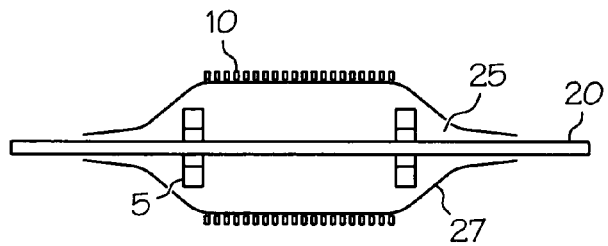
FIG. 3 is a side view of a catheter with a hub located under the cone portions of the balloon.

As shown in FIGS. 1-3, a hub 5 may be located at the proximal end of the stent retaining region and at least one other hub may be located at the distal end of the stent retaining region. The hubs 5 can also be located under the cone portions 27 of the balloon 25 as shown in FIG. 3 which show the balloon and stent in an expanded state.

The retaining device can be at least one sheath which is capable of preventing the stent or medical device from self-expanding. During and/or immediately after deployment of the stent the sheath or sheaths as described herein can be pulled back while the catheter remains substantially fixed or the catheter itself can be retracted in order to allow the stent to expand. The stents in FIGS. 4-12 and 15-23b can be self-expanding stents that expand without a balloon. However, in these figures the stent may be mounted on a balloon rather than mounted on a catheter.

Figure 4A:
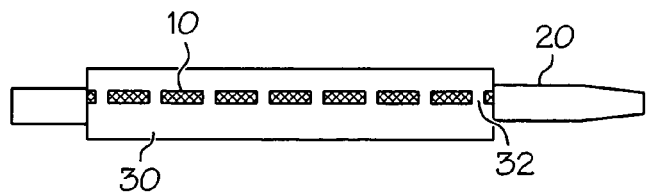
FIG. 4a is a side view of a catheter with a sheath retaining a stent.

In FIGS. 4a and 5a, the sheath 30 is held about a stent 10 by EAP sheath connectors 32 in an activated state which retains the stent 10 to the catheter 20. The sheath connectors 32 can hold the ends of the sheath 30 in close proximity when activated. The connectors 32 can do this by curling inward while gripping the ends of the sheath. Connectors 32 can also curl to engage oppositely curled portions at the end of the sheath 30. The sheath 30 can also be restrained by multiple protrusions which extend from the connectors 32 and engage loops or ridges on the sheath 30.

Figure 4B:
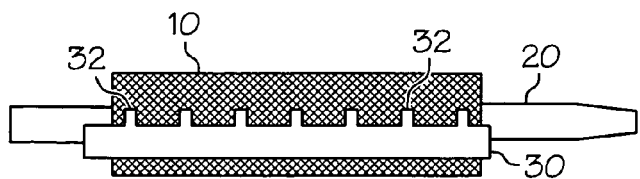
FIG. 4b is a side view of a catheter with a sheath with an expanded stent.

Upon inactivation, as shown in FIGS. 4b and 5b, the connectors 32 can release the ends of the sheath 30. By releasing the ends of the sheath the stent 10 is free to expand. The sheath 30 as shown in FIGS. 4b and 5b can shorten in length. In some instances the shortening is less than that shown, in others more.

In FIG. 6a, the sheath 30 comprises a rolling membrane 33 coated with an electroactive polymer 34. The rolling membrane 33 of the self expanding stent delivery system (SDS) 35 can aid in attaching the stent 10 to the SDS temporarily until deployed. This may substantially reduce jumping of the stent during deployment. This can be done by providing an EAP coating 34 on the inner diameter of the rolling membrane 33. The EAP is entrapped between the stent struts 10 and secures the stent 10 in place during deployment.

As shown in FIG. 6b, the outer sheath 30 can then be pulled back. The rolling sheath 33 can then retract allowing the stent 10 to deploy into the lumen 41 and released from the inner catheter shaft 20. The partial retraction of the rolling sheath 33 as shown can be due to the outer sheath 30 retracting and acting on the rolling sheath or due to activation of the EAP portion of the rolling membrane 33. The partial expansion of stent 10 can further affect the retraction of the rolling sheath 33.

As shown in FIG. 6c, activation of the EAP portion of the rolling sheath 33 can result in the rolling sheath 33 fully retracting such that the stent 10 can fully deploy into the lumen 41.

In FIGS. 7-8, a sheath 30 has an inner portion 30a, multiple gold longitudinal strips 30b deposited about the circumference of the inner portion, and EAP strips 30c disposed on the gold strips 30b. The inner portion 30a can be composed of a soft polymer such as Tecothane (PU). In the inactivated state as shown in FIG. 7 the EAP strips substantially conform to the shape of the gold strips 30b. In the activated state as shown in FIG. 8, the EAP portions 30c bend into a V-like shape such that the sheath inner portion 30a is drawn inward and forms wing portions 9. It should be noted that the number of strips 30b,c is variable and can for example range between 3-40. Less or more strips can also be used. It should be further noted that other metals can be used in place of gold.

As shown in FIG. 9a, a sheath 30 comprising EAP can be in the form of a sheet capable of being rolled about a stent 10 in an inactived state and capable of unrolling from about the stent in the activated state. As the EAP sheath 30 is actuated the sheath begins to unroll and open as shown in FIG. 9b. This can allow the stent 10 to expand evenly along its length. This evenness of expansion, particularly longitudinally, can minimize the amount of length change upon expansion and can greatly reduce the possibility of the stent "jumping" upon delivery.

As shown in FIGS. 10a and 10b, an EAP retaining sheath 30 retains a self-expanding stent 10 to the inner shaft 20 of a SDS. When the stent 10 is in the crimped state and the sheath 30 is in the inactivated state (FIG. 10a), the stent 10 exerts the maximum force to the sheath 30 which in turn results in the maximum deployment force. When the EAP retention sheath 30 is activated as shown in FIG. 10b, the diameter of the sheath 30 increases to a predeployed state that is larger than the crimped state. In this larger diameter state, the force the stent 10 exerts on the sheath 30 is reduced. This in turn reduces the sheath withdrawal force. Thus, when the sheath 30 is retracted there is less likelihood for the stent 10 to jump during deployment because the stent has less stored energy once it has partially expanded than when fully crimped.

A stent delivery system 35, as shown in FIG. 10c, has a second sheath 39 disposed about an inner sheath 30 comprising an EAP. As shown, both sheaths 30, 39 cover the self expanding stent 10 while tracking the catheter to the deployment location. During this time, the inner EAP sheath 30 can be in an inactivated state. When the SDS 35 reaches the deployment location, the outer sheath 39 can be retracted allowing the stent 10 to partially self expand against the inner EAP sheath 30 as shown in FIG. 10d. The EAP sheath 30 can then be activated causing the EAP sheath 30 to radially expand thereby allowing the distal end of the stent 10 to contact the vessel wall 41 as shown in FIG. 10e. The EAP sheath 30 can then be retracted allowing the stent 10 to fully deploy.

Referring to FIGS. 11a and 11b, an EAP sheath 30 having an EAP portion 34 may be disposed about the length of the stent 10 in the inactivated state and roll off the stent when activated. In FIG. 11a the sheath 30 is in an inactivated state. In FIG. 11b electrical activation of the EAP sheath 30 results in the sheath 30 curling back and allowing the stent 10 to deploy. This can provide for a more precise stent release. Here The EAP portion 34 of the sheath 30 can be activated to change geometry such that the EAP portion 34 lengthens more than the remainder of the sheath 30 resulting in the sheath 30 curling or rolling back. By this method, a short length stent 10 would not be at risk of an unwanted movement away from the balloon body prior to full vessel stent dilation. This undesirable movement can occur with passive sock designs. The EAP sheath 10 could have both radial and longitudinal break points allowing for segmented roll back of the material in sections. A reversal of the electrical signal would cause the EAP sheath members to unroll and minimize fluid deflation time and catheter withdrawal profiles.

Further regarding FIGS. 11a and 11b, it should be noted that the EAP portion 34 could be placed on the outside of the sheath 30 such that inactivation of the EAP portion 34 rather than activation of the EAP portion results in the sheath 30 rolling or curling back to deploy the stent 10. It should be further noted that in some embodiments the EAP sheath does not have an EAP portion 34 that is a separate layer as illustrated in FIGS. 11a and 11b; the sheath 30 can be comprised of EAP such that in transitioning between the activated and the inactivated state the sheath 30 changes geometry so as to curl or roll back to allow the stent 10 to deploy.

As shown in FIGS. 12a-12b, the retaining device can be one or more EAP layers or portions 34 disposed about the inner shaft 20 of the catheter 35. The layer(s) 34 can extend along the entire length of the stent 10 or be disposed in distinct locations between stent strut members 10. In the inactivated state of FIG. 12a, the one or more EAP layers or portions 34 do not exert a force on the stent struts 10 capable of retaining the stent to the inner catheter 20. Thus, the stent is capable of deploying when outer sheath 30 is retracted. In some instances the portions 34 when inactivated are not in contact with the stent struts, yet when activated as shown in FIG. 12b, the EAP layer 34 can shift or expand such that it at least partially fills the space between adjacent struts 10 such that the EAP layer or portion 34 exerts force on adjacent struts 10 capable of retaining the stent 10 to the inner catheter 20. In some embodiments a layer 34 can extend along the entire length of the stent 10 and the stent is pressed into the layer such that portions under the stent strut members 10 are flatter than the portions ("34" in FIG. 12a) between the stent strut members. In some embodiments the EAP layer or layers can be a pattern comprising thickened dot or strip portions that when actuated extend(s) into the spaces 33 between the struts.

As shown in FIGS. 13a-c the retaining device can be a sock 44 comprising an EAP portion. In FIG. 13a, the sock 44 covers at least a portion of a balloon 42 or a catheter shaft and retains the stent 10 thereto in the activated state. In the inactivated state, as shown in FIG. 13b, the sock moves off of the stent 10 to allow stent expansion and deployment. In the event that the procedure is aborted, the EAP socks can again be activated to protect the ends of stent 10 from catching on portions of the SDS (e.g. guide catheter) during withdrawal as illustrated in FIG. 13c. It should be noted that one or more socks can be used in the embodiments above. The socks 44 can be used with either a self-expanding and/or a balloon expandable stent. In some embodiments, the EAP sock or sheath 30 retracts like an accordion in order to deploy the stent. In another embodiment, the EAP portion acts as a pull back mechanism for retracting a sock or sheath.

In some embodiments as in FIG. 14a, EAP material 46 is disposed on the body of the balloon 42 to restrain expansion of the stent. As shown in FIG. 14b the EAP material 46 is in a first state wherein the stent can be released from the balloon 42. Upon transitioning to the second state, as shown in FIG. 14c, the stent struts 47 are held to the balloon 42 thereby restraining the stent to the balloon.

Figure 15A:
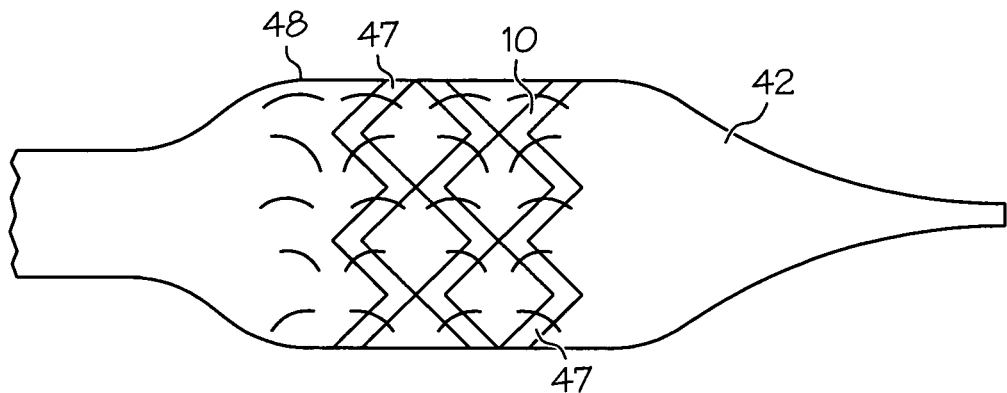
Figure 15B:
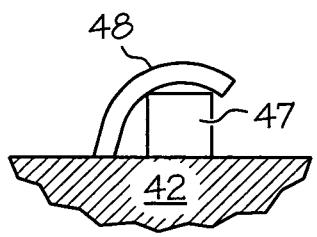
Figure 15C:
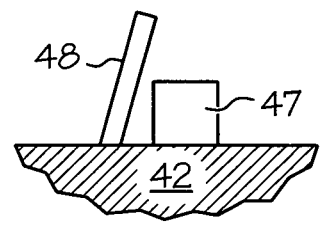

As shown in FIG. 15a, the retaining device can comprise a hook and loop configuration. In such a configuration, a stent 10 is disposed about a balloon 42. The balloon 42 can have fingers/hooks 48 comprising EAP. As shown in FIG. 15b, a finger/hook 48 can extend from the balloon 42 and bend over the strut 47 of stent 10 when actuated by activating or inactivating the hook 48 having EAP. When actuated the stent 10 is restrained from expanding as strut 47 is held to the balloon. FIG. 15c illustrates the finger/hook 48 when unactuated. In the unactuated state the stent 10 is free to expand or be released from the balloon 42 as the hook 48 is no longer holding the strut 47 to the balloon.

Figure 15D:
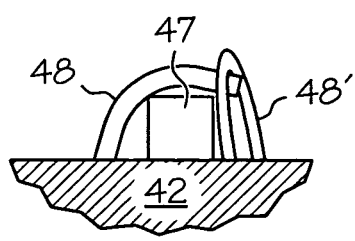
Figure 15E:
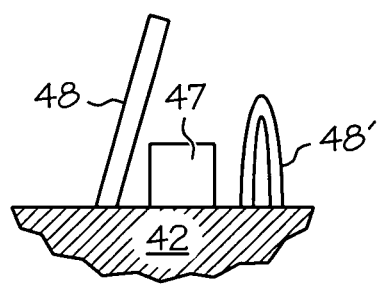

In FIG. 15d, the finger/hook 48 in the actuated state is hooked within a loop 48' extending from the balloon 42. The loop 48' can also comprise EAP be actuated in the same manner as hook 48. In this configuration the strut 47 of stent 10 is restrained from being released from balloon 42. In FIG. 15e both the hook 48 and loop 48' are not actuated and the strut 47 of stent 10 is free to be released from the balloon 42. It should be noted that in FIGS. 15a-15e a stent is mounted about a balloon. The stent in FIGS. 15a-15e can be mounted about a catheter shaft. The loops and/or hooks can also be designed to break during activation or inactivation.

As shown in FIG. 16 a cylinder 52 comprising EAP is disposed within a sheath wall 32 as shown in cross-section. The sheath wall 32 can be at least partially constructed of a hard polymer and can include holes 31 which allow electrolyte access during activation of the EAP cylinder 52. As shown, a counter electrode 36, perhaps comprising gold, can be disposed about the sheath wall 32. The EAP cylinder 52 can be disposed on or about a polymeric tube 37 having an outer metallic layer 38. The outer metallic layer 38 can be gold deposited on the polymeric tube 37. A pliable tube/sack 33 filled with a fluid 34 (e.g. water) is disposed within the EAP cylinder 52 and the polymeric tube 37. The pliable tube can be constructed of a closed thin film silicone rubber tube.

The catheter tip portion 2 of FIG. 16a is shown in FIGS. 16b and 16c in longitudinal cross-section. As illustrated, the tube 33 and cylinder 52 can be disposed proximal to the stent 10. In some embodiments, a small disc 39 is placed between the EAP cylinder 52 and the loaded stent 10. As shown in FIG. 16b the EAP cylinder 52 is in the inactivated state wherein the pliable tube 33 is not being substantially acted upon by the cylinder 52. As shown in FIG. 16c, actuating the EAP cylinder 52 will compress the fluid filled pliable tube 33 and extrude it out into the distal axial direction. The disc 39 between the EAP cylinder 52 and the loaded stent 10 will act to deploy the stent 10 by pushing it out the end of the catheter.

The EAP cylinder 52 can also be considered to comprise multiple layers as well and can be made by sputtering a gold layer on top of a first polymeric tube (soft compliant material). An EAP layer can then be polymerized on top of the gold layer. The cylinder 52 is then placed inside of the catheter.

Electrolyte access can be provided by holes 31 in the outside of the sheath wall 32 in the area that the EAP cylinder 52 will be housed. The outer surface of the sheath wall 32 can be coated with counter electrode 36. Applying a voltage will drive ions in or out of the EAP cylinder 52 thereby compressing or releasing the fluid tube 33 and extruding it out in a distal direction. The EAP material can develop a 3-5 MPa pressure. If the delivery sheath has a 2 mm diameter, about 10 N of force can be developed to act on the sliding disc 39. The actuation distance is purely defined by the length of the EAP cylinder 52 and its volume displacement. So, with a 20% expansion of the EAP the stent 10 can be driven 10 mm forward by displacing 31 cubic mm of fluid 34. If an EAP cylinder 52 has an outer diameter of 2 mm and a wall thickness of 500 micrometer, the internal diameter is about 1 mm. An expansion of 100 micrometers inwards will result in a volume of 31 cubic mm if the EAP cylinder is about 10.9 cm long. This may allow the system to use a relatively soft catheter.

EAP socks or bumpers can be used for the main branch as well as the side branch of the stent and/or catheter. In FIGS. 17a-h bifurcated assemblies 35 having a bifurcated stent 10 with EAP bumpers 7 shown.

Figure 17C:
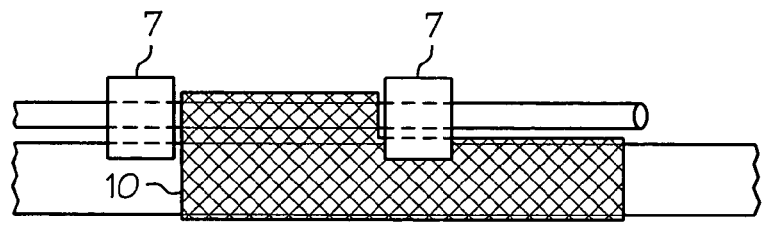
Figure 17D:
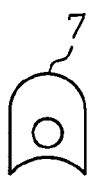
Figure 17E:
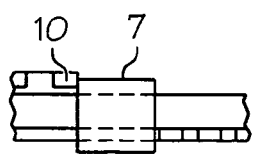
Figure 17F:
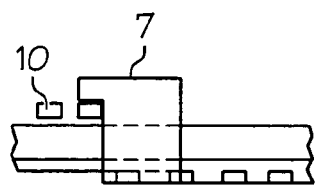

The EAP bumpers 7 as shown in FIGS. 17a,e can be in an inactivated state which has a profile smaller than that of the loaded stent 10. Upon activation the EAP bumper 7 can expand to provide protection to the stent edges of the side branch portion 41b by increasing in diameter as shown in FIGS. 17c,f. As shown in FIG. 17f the EAP bumper can transform such that a portion of the bumper 7 extends over the stent 10 to restrain expansion of the stent. Upon inactivation as in FIGS. 17a,e the stent 10 can be free to expand.

Figure 17G:
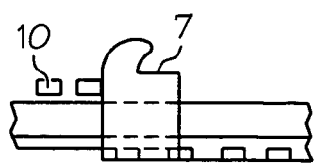

FIG. 17f in some embodiments represents an inactivated state wherein a portion of the bumper 7 extends over the stent 10 and upon activation the EAP bumper 7 changes geometry such that the portion rolls or curls back away from the stent 10 as shown in FIG. 17g. The portion of the bumper 7 that extends over the stent 10 can extend over a larger percentage of the length of the stent 10 than is shown in FIG. 17f and in some embodiments extends over the entire length of the stent 10.

Figure 17H:
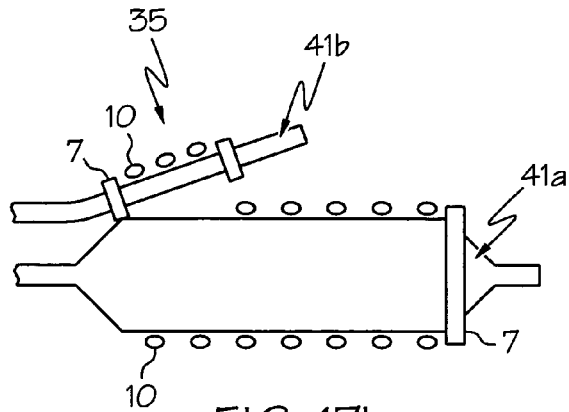

In some embodiments the bumpers 7 are disposed about both the main branch 41a and the side branch 41b of the assembly 35. The EAP bumpers when transitioning from the inactivated state to the activated state can increase in diameter and provide edge protection for the stent 10. FIG. 17h illustrates a bifurcated SDS 35 having bumpers 7 on both the main branch 41a and the side branch 41b.

In the embodiments of FIGS. 17a-h, socks comprising EAP can be used in addition to or rather than the EAP bumpers 10 such that when in the inactivated state the socks extend over a portion of the bifurcated stent thereby securing the stent 10 to the catheter. Upon activation of the EAP socks, the socks can retract in order to allow the stent to fully expand and deploy. As noted above, in all the embodiments of the application, securement can occur in either the activated or the inactivated state and release/deployment can result respectively in transitioning to the inactivated or activated state.

As illustrated in FIGS. 18a-e, the retaining device can be one or more EAP layers or portions 34 disposed about the inner shaft 20 of the catheter 35. The layer(s) 34 can extend along the entire length of the stent 10 or be disposed in distinct locations, such as between stent strut members 10. In the inactivated state of FIG. 18a, the one or more EAP layers or portions 34 do not exert a force on the stent struts 10 capable of retaining the stent to the inner catheter 20. Thus, the stent is capable of deploying when outer sheath 30 is retracted. The portions 34 need not be in contact with the stent struts in the inactivated state. When activated in FIG. 18b, the EAP layers can shift or expand such that it mushrooms between the stent struts 10 and extends over the struts so as to cover at least a portion of the strut as shown with more detail in FIG. 18c. In the activated state the EAP portion 34 retains the stent 10 to the inner catheter 20.

In FIG. 19a, a band 53 is strapped around the catheter or balloon. Neck portions 54 having EAP head portions 34 extend from the band 53. The EAP head portions 34/34' are shown in an inactivated state (34) and an activated state (34'), respectively. In the inactivated state the stent 10 can expand as the EAP 34 is small enough to pass through the cells or space between adjacent struts of the stent 10. In the activated state the EAP portion 34' is configured such that it cannot pass through the space between adjacent struts of the stent 10. Thus in the activated state the stent 10 is retained from expanding and deploying from the SDS.

Multiple EAP portions 34 can be disposed about the catheter shaft 20 as shown in the cross-sectional view of FIG. 19b. It should be noted that some of the EAP portions 34 can be activated at the same or at different times from other EAP portions 34. It should be further noted that in some embodiments the band 53 and/or neck portions 54 comprise EAP portions. In some embodiments, neither the band 53 nor the neck portions comprise EAP portions.

A pseudo stent pattern can be engraved in the region about which the stent will be disposed. EAP portions can be included in areas having the pseudo stent pattern where stent 10 is to be positioned. In FIG. 20, a stent 10 is disposed about an inner catheter portion 20 having a pattern that matches that of the stent 10. The stent 10 is covered by an outer catheter tube/sheath 30. An enlarged cross-section 21' of inner catheter portion 20 is shown in FIG. 21a (outer sheath 30 not shown) and illustrates a slot 22 within the wall of the inner catheter portion 20. The inner catheter portion 20 in some embodiments has a layer of metallic material 23 disposed thereon (e.g. gold). An EAP material 24 can be disposed upon the layer of metallic material 23. The slot 22 as shown in FIGS. 21a,b is a portion of the pattern within the inner catheter portion 20 that substantially matches the pattern of the stent configuration. As shown in the drawings, the metallic material 23 and the EAP material 24 are also disposed within the slot 22. The stent struts 10 can also be disposed within the slot 22. Various means can be used to do this, including pushing the stent 10 into the pattern/slot 22 using a tapered tube that squeezes the stent on and into the pattern/slot of the inner catheter portion 20.

As shown in FIG. 21*a*, the EAP layer 24 is activated and the stent strut 10 is squeezed by the thickened EAP layer 24 such that the stent 10 is constrained from self expanding. When the EAP layer 24 is inactivated, the EAP layer thins out and allows space to develop within slot 22 such that the stent strut 10 can pop out of the slot. Upon withdrawal of the outer sheath 30 the stent can then expand and deploy.

As an example, the inner catheter portion 20 can be a polymer tube (e.g. nylon 12) in which a pattern substantially matching that of a stent is laser ablated into the wall of the tube. The stent 10 can have struts with a thickness of 80 micrometer and a height of 80 micrometer. The slot pattern 22 can be 120 micrometer deep for tube wall thicknesses of 240 micrometer or more. The inner catheter portion 20 can be sputtered with a gold layer 23 and a 20 micrometer thick EAP layer 23 can be deposited thereon. In some embodiments, the slot pattern 22 can be fashioned so as to be about 25 micrometers wider on both sides than the stent 10.

As shown in FIGS. 22*a,b* and 23*a,b*, an EAP umbrella 30 can be disposed distal of a stent. The EAP umbrella 30 can be activated before release to form a bumper in the vessel to prevent a stent from jumping past a treatment site.

As shown in FIGS. 22*a-b* and 23*a-b*, the umbrella 30 can comprise an inner portion 30*a*, multiple gold longitudinal strips 30*b* can be deposited about the circumference of the inner portion, and EAP strips 30*c* can be disposed on the gold strips 30*b*. The inner portion 30*a* can be composed of a soft polymer such as Tecothane (PU). The proximal end of the umbrella 30 is free to expand away from the guide wire 3 while the distal end is connected to the guide wire 3. In the inactivated state as shown in FIGS. 22*b* and 23*b*, the EAP strips are slightly curved about the inner portion 30*a* and the gold strips 30*b*. The strips in the inactivated state can also be substantially straight. In the activated state as shown in FIGS. 22*a* and 23*a*, the EAP portions 30*c* bend into a V-like shape such that the inner portion 30*a* is drawn inward and forms wing portions 9. It should be noted that the number of strips 30*b,c* is variable and can for example range between 3-40. It should be further noted that other metals can be used in place of gold. Additionally, in some embodiments all portions of the umbrella 30 are not completely distal to a stent such that at least a portion of the umbrella 30 is disposed about at least a portion of the stent.

The invention also pertains to an EAP opening mechanism for a distal filter. As shown in FIG. 24*a* an EAP expander ring 49 is disposed about a guide wire 3 and disposed beneath a wire portion/filter 51. When in the inactivated state the wire portion 51 is collapsed about guide wire 3. The EAP expander ring 49 is placed near a point where the struts of the wire portion 51 meet. When the EAP ring 49 is activated the ring increases in diameter and pushes the struts of the wire filter 51 outward such that when disposed within a vessel lumen the struts would make contact with the vessel wall. When expanded as shown in FIG. 24*b*, the wire filter can provide down stream protection from material which has been dislodged from the treatment site thereby avoiding the use of a recovery sheath. When the expander ring is inactivated again the struts can collapse the wire filter back down to the wire in preparation for removal. In some embodiments a shape memory material such as Nitinol or a spring steel can be used in the construction of the wire filter.

As presented within this specification, a change in shape of the EAP material can also constitute merely a change in volume.

The present invention may be incorporated into both of the two basic types of catheters used in combination with a guide wire, commonly referred to as over-the-wire (OTW) catheters and rapid-exchange (RX) catheters. The construction and use of both over-the-wire and rapid-exchange catheters are well known in the art.

It should be understood that the embodiments as described above can retain a stent in an activated state and release it in an inactivated state or it can retain a stent in the inactivated state and release it in the activated state.

The present invention may also be incorporated into assemblies for treatment at a lumen bifurcation. Examples of such systems are shown and described in U.S. patent application Ser. No. 10/375,689, filed Feb. 27, 2003 and U.S. patent application Ser. No. 10/657,472, filed Sep. 8, 2003 both of which are entitled Rotating Balloon Expandable Sheath Bifurcation Delivery; U.S. patent application Ser. No. 10/747,546, filed Dec. 29, 2003 and entitled Rotating Balloon Expandable Sheath Bifurcation Delivery System; U.S. patent application Ser. No. 10/757,646, filed Jan. 13, 2004 and entitled Bifurcated Stent Delivery System; and U.S. patent application Ser. No. 10/784,337, filed Feb. 23, 2004 and entitled Apparatus and Method for Crimping a Stent Assembly; the entire content of each of which are incorporated herein by reference.

Embodiments of the present invention can be incorporated into those shown and described in the various references cited above. Likewise, embodiments of the inventions shown and described therein can be incorporated herein.

In some embodiments the stent or other portion of the assembly, including the sheath 28, may include one or more areas, bands, coatings, members, etc. that is (are) detectable by imaging modalities such as X-Ray, MRI or ultrasound. In some embodiments at least a portion of the stent, sheath and/or adjacent assembly is at least partially radiopaque.

A therapeutic agent may be placed on the stent 34 and/or the sheath 28 in the form of a coating. Often the coating includes at least one therapeutic agent and at least one polymer. A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the polymer agent may be a polystyrene-polyisobutylene-polystyrene triblock copolymer (SIBS), polyethylene oxide, silicone rubber and/or any other suitable substrate.

The above materials throughout the application are intended for illustrative purposes only, and not as a limitation on the scope of the present invention. Suitable polymeric materials available for use are vast and are too numerous to be listed herein and are known to those of ordinary skill in the art.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

With this description, those skilled in the art may recognize other equivalents to the specific embodiment described herein. Such equivalents are intended to be encompassed by the claims attached hereto.

The invention claimed is:
1. A catheter comprising:
a medical device receiving region;
a stent disposed about the medical device receiving region in a reduced state for delivery; and
a stent retaining device which is activatable to release the stent,
wherein the retaining device comprises an electroactive polymer, the retaining device having different first and second shapes corresponding to activated and inactivated states of the electroactive polymer, and the retaining device configured to effect release of the stent as a result of a shape change induced by activation or inactivation of the electroactive polymer therein;
wherein the retaining device is at least one sheath having a first portion and a second portion;
wherein, in the inactivated state, the first portion of the at least one sheath is disposed about a length of the stent and, in the activated state, the first portion of the at least one sheath is curled back such that the first portion of the at least one sheath is disposed about the second portion of the at least one sheath.

* * * * *